United States Patent
Bates et al.

(10) Patent No.: US 12,412,663 B2
(45) Date of Patent: Sep. 9, 2025

(54) SYSTEMS AND METHODS FOR AUDIO MEDICAL INSTRUMENT PATIENT MEASUREMENTS

(71) Applicant: AdviNow, Inc., Paradise Valley, AZ (US)

(72) Inventors: James Stewart Bates, Paradise Valley, AZ (US); Kristopher Perry, Phoenix, AZ (US); Chaitanya Prakash Potaraju, Tempe, AZ (US); Pranav Bhatkal, Tempe, AZ (US); Aditya Shirvalkar, Tempe, AZ (US); Tristan Royal, Phoenix, AZ (US)

(73) Assignee: AdviNow, Inc., Paradise Valley, AZ (US)

( * ) Notice: Subject to any disclaimer, the term of this patent is extended or adjusted under 35 U.S.C. 154(b) by 0 days.

(21) Appl. No.: 18/607,522

(22) Filed: Mar. 17, 2024

(65) Prior Publication Data
US 2024/0266055 A1 Aug. 8, 2024

Related U.S. Application Data

(62) Division of application No. 17/827,962, filed on May 30, 2022, now Pat. No. 11,935,656, which is a (Continued)

(51) Int. Cl.
*G08B 21/00* (2006.01)
*A61B 5/0205* (2006.01)
(Continued)

(52) U.S. Cl.
CPC ........... *G16H 50/20* (2018.01); *A61B 5/0205* (2013.01); *A61B 5/316* (2021.01); *A61B 7/02* (2013.01);
(Continued)

(58) Field of Classification Search
CPC ........ G16H 50/20; G16H 50/30; G16H 40/63; A61B 5/0205; A61B 5/316; A61B 7/02;
(Continued)

(56) References Cited

U.S. PATENT DOCUMENTS 7,244,230 B2 * 7/2007 Duggirala ................ A61B 8/56
600/443
9,208,287 B2 * 12/2015 Waterson ............... G16H 50/20
(Continued)

*Primary Examiner* — Toan N Pham
(74) *Attorney, Agent, or Firm* — North Weber & Baugh; Michael North

(57) ABSTRACT

Presented are systems and methods for the accurate acquisition of medical measurement data of a body part of patient. To assist in acquiring accurate medical measurement data, an automated diagnostic and treatment system provides instructions to the patient to allow the patient to precisely position a medical instrument in proximity to a target spot of a body part of patient. For a stethoscope examination, the steps may include utilizing object tracking to determine if the patient has moved the stethoscope to a recording site; utilizing DSP processing to confirm that the stethoscope is in operation, utilizing DSP processing to generate a pre-processed audio sample from a recorded audio signal; using machine learning (ML) to determine if a signal of interest (SOI) is present in the pre-processed sample. If SoI is present, using ML to evaluate characteristics in the signal which indicate the presence of abnormalities in the organ being measured.

11 Claims, 11 Drawing Sheets

Related U.S. Application Data division of application No. 15/913,822, filed on Mar. 6, 2018, now Pat. No. 11,348,688.

(51) Int. Cl.
  *A61B 5/316* (2021.01)
  *A61B 7/02* (2006.01)
  *G16H 50/20* (2018.01)
  *A61B 5/00* (2006.01)
  *A61B 5/024* (2006.01)
  *G16H 50/30* (2018.01)

(52) U.S. Cl.
  CPC ............ *A61B 5/0033* (2013.01); *A61B 5/024* (2013.01); *A61B 5/6897* (2013.01); *G16H 50/30* (2018.01)

(58) Field of Classification Search
  CPC ..... A61B 5/0033; A61B 5/024; A61B 5/6897; A61B 5/061; A61B 5/684
  See application file for complete search history.

(56) References Cited

U.S. PATENT DOCUMENTS

| | | | |
|---|---|---|---|
| 11,935,656 B2* | 3/2024 | Bates | G16H 50/20 |
| 2011/0144451 A1* | 6/2011 | Robertson | G16H 40/67 |
| | | | 600/300 |
| 2014/0164022 A1* | 6/2014 | Reed | G16H 40/63 |
| | | | 705/3 |
| 2019/0355149 A1* | 11/2019 | Avendi | G06T 7/74 |
| 2022/0044802 A1* | 2/2022 | Patel | G16H 40/63 |

* cited by examiner

SYSTEMS AND METHODS FOR AUDIO MEDICAL INSTRUMENT PATIENT MEASUREMENTS

CROSS REFERENCE TO RELATED PATENT APPLICATIONS

The present application a divisional of and claims priority benefit to co-pending and commonly-assigned U.S. patent application Ser. No. 17/827,962 entitled "Systems and Methods for Audio Medical Instrument Patient Measurements", filed on May 30, 2022, listing James Stewart Bates, Kristopher Perry, Chitanya Prakash Potaraju, Pranav Bhatkal, Aditya Shirvalkar, and Tristan Royal as inventors, which claims priority to U.S. patent application Ser. No. 15/913,822, entitled "Systems and Methods for Audio Medical Instrument Patient Measurements", filed on Mar. 6, 2018, listing as inventors James Stewart Bates, Kristopher Perry, Chitanya Prakash Potaraju, Pranav Bhatkal, Aditya Shirvalkar, and Tristan Royal as inventors, which applications are incorporated by reference herein in their entireties and for all purposes.

BACKGROUND

Technical Field

The present disclosure relates to computer-assisted health care, and more particularly, to systems and methods for providing a computer-assisted medical diagnostic architecture in which a patient is able to perform certain medical measurements with the assistance of a medical kiosk or medical camera system.

BACKGROUND OF THE INVENTION

One skilled in the art will recognize the importance of addressing the ever-increasing cost of providing consistent, high-quality medical care to patients. Governmental agencies and insurance companies are attempting to find solutions that reduce the cost of medical care without significantly reducing the quality of medical examinations provided by doctors and nurses. Through consistent regulation changes, electronic health record changes and pressure from payers, both health care facilities and providers are looking for ways to make patient intake, triage, diagnosis, treatment, electronic health record data entry, treatment, billing, and patient follow-up activity more efficient, provide better patient experience, and increase the doctor to patient throughput per hour, while simultaneously reducing cost.

The desire to increase access to health care providers, a pressing need to reduce health care costs in developed countries and the goal of making health care available to a larger population in less developed countries have fueled the idea of telemedicine. In most cases, however, video or audio conferencing with a doctor does not provide sufficient patient-physician interaction that is necessary to allow for a proper medical diagnosis to efficiently serve patients.

What is needed are systems and methods that ensure reliable remote or local medical patient intake, triage, diagnosis, treatment, electronic health record data entry/management, treatment, billing and patient follow-up activity so that physicians can allocate patient time more efficiently and, in some instances, allow individuals to manage their own health, thereby, reducing health care costs.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

Figure 1:
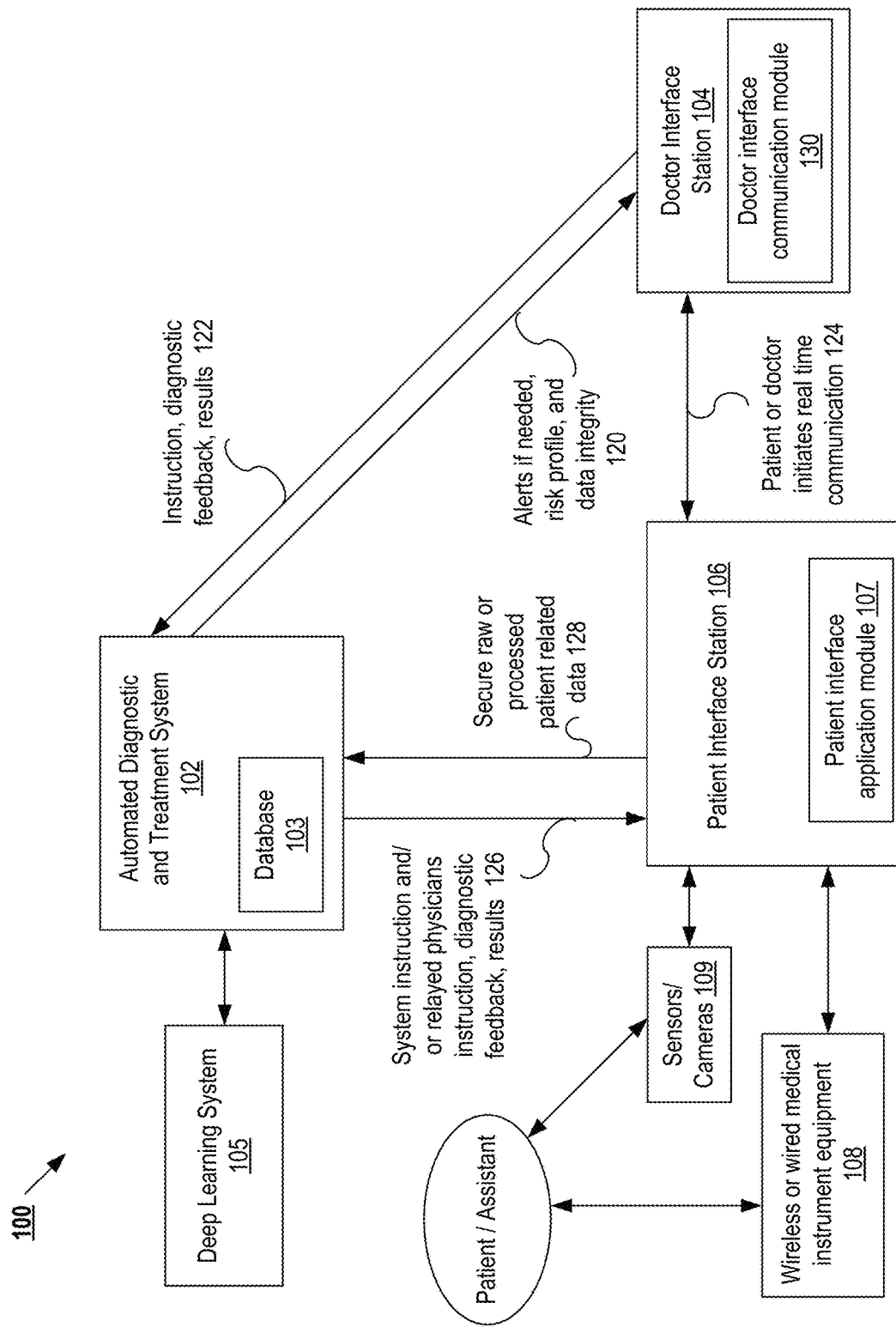
FIG. 1 illustrates an exemplary medical diagnostic system according to embodiments of the present disclosure.

In the following description, for purposes of explanation, specific details are set forth in order to provide an understanding of the disclosure. It will be apparent, however, to one skilled in the art that the disclosure can be practiced without these details. Furthermore, one skilled in the art will recognize that embodiments of the present disclosure, described below, may be implemented in a variety of ways, such as a process, an apparatus, a system, a device, or a method on a tangible computer-readable medium.

Elements/components shown in diagrams are illustrative of exemplary embodiments of the disclosure and are meant to avoid obscuring the disclosure. It shall also be understood that throughout this discussion that components may be described as separate functional units, which may comprise sub-units, but those skilled in the art will recognize that various components, or portions thereof, may be divided into separate components or may be integrated together, including integrated within a single system or component. It should be noted that functions or operations discussed herein may be implemented as components/elements. Components/elements may be implemented in software, hardware, or a combination thereof.

Furthermore, connections between components or systems within the figures are not intended to be limited to direct connections. Rather, data between these components may be modified, re-formatted, or otherwise changed by intermediary components. Also, additional or fewer connections may be used. Also, additional or fewer connections may be used. It shall also be noted that the terms "coupled"

"connected" or "communicatively coupled" shall be understood to include direct connections, indirect connections through one or more intermediary devices, and wireless connections.

Reference in the specification to "one embodiment," "preferred embodiment," "an embodiment," or "embodiments" means that a particular feature, structure, characteristic, or function described in connection with the embodiment is included in at least one embodiment of the disclosure and may be in more than one embodiment. The appearances of the phrases "in one embodiment," "in an embodiment," or "in embodiments" in various places in the specification are not necessarily all referring to the same embodiment or embodiments. The terms "include," "including," "comprise," and "comprising" shall be understood to be open terms and any lists that follow are examples and not meant to be limited to the listed items. Any headings used herein are for organizational purposes only and shall not be used to limit the scope of the description or the claims.

Furthermore, the use of certain terms in various places in the specification is for illustration and should not be construed as limiting. A service, function, or resource is not limited to a single service, function, or resource; usage of these terms may refer to a grouping of related services, functions, or resources, which may be distributed or aggregated.

In this document, the term "sensor" refers to a device capable of acquiring information related to any type of physiological condition or activity (e.g., a biometric diagnostic sensor); physical data (e.g., a weight); and environmental information (e.g., ambient temperature sensor), including hardware-specific information. The term "position" refers to spatial and temporal data (e.g. orientation and motion information). The position data may be, for example, but without limitations, 2-dimensional (2D), 2.5-dimensional (2.5D), or true 3-dimensional (3D) data representation. "Doctor" refers to any health care professional, health care provider, physician, or person directed by a physician. "Patient" is any user who uses the systems and methods of the present invention, e.g., a person being examined or anyone assisting such person. The term illness may be used interchangeably with the term diagnosis. As used herein, "answer" or "question" refers to one or more of 1) an answer to a question, 2) a measurement or measurement request (e.g., a measurement performed by a "patient"), and 3) a symptom (e.g., a symptom selected by a "patient").

FIG. 1 illustrates an exemplary medical diagnostic system according to embodiments of the present disclosure. Diagnostic system 100 comprises automated diagnostic and treatment system 102, patient interface station 106, doctor interface station 104, deep learning system 105, sensors/cameras 109 and medical instrument equipment 108. Deep learning system 105 may include, for example, but without limitations, deep convolution neural network (DCNN), Multi-layer preceptrons (MLP), Fully Convolutional Networks (FCNs), Capsule Networks, and artificial neural networks (A-NNs). Both patient interface station 106 and doctor interface station 104 may be implemented into any tablet, computer, mobile device, or other electronic device. Deep learning system 105 utilizes virtual, augment, or mixed reality to assist the automated diagnostic and treatment system 102 to obtain improved medical measurements by the medical instrument equipment 108. Deep learning may be a name referring to the use of "stacked neural networks"; that is, networks composed of several layers. The layers are made of nodes, where a node is just a place where computation occurs and is loosely patterned on a neuron in the human brain. The neuron in the brain fires when it encounters sufficient stimuli. Deep learning system 105 may be used in computer vision and have also have been applied to acoustic modeling for automatic speech recognition (ASR). Automated diagnostic and treatment system 102 may be referred to as an automated diagnostic system, or simply diagnostic system.

Patient interface station 106 comprises patient interface application module 107 and is coupled to sensors/cameras 109. In turn, sensors/cameras 109 may monitor and may capture images of the patient/assistant. Patient interface station 106 receives from the automated diagnostic and treatment system 102 system instruction and/or relayed physicians instruction, diagnostic feedback, results 126. Patient interface station 106 sends to the automated diagnostic and treatment system 102 secure raw or processed patient-related data 128. Patient interface station 106 also provides interfaces between sensors/cameras 109, located in the patient interface station 106, and the patient/assistant. Patient interface station 106 also provides interfaces to medical instrument equipment 108. Medical instrument equipment 108 may be, for example, but without limitations, a stethoscope, ophthalmoscope, intraoral camera, auriscope, or otoscope.

Medical instrument equipment 108 is designed to collect mainly diagnostic patient data, and may comprise one or more diagnostic devices, for example, in a home diagnostic medical kit that generates diagnostic data based on physical and non-physical characteristics of a patient. It is noted that diagnostic system 100 may comprise additional sensors and devices that, in operation, collect, process, or transmit characteristic information about the patient, medical instrument usage, orientation, environmental parameters such as ambient temperature, humidity, location, and other useful information that may be used to accomplish the objectives of the present invention.

In operation, a patient may enter patient-related data, such as health history, patient characteristics, symptoms, health concerns, medical instrument measured diagnostic data, images, and sound patterns, or other relevant information into patient interface station 106. The patient may use any means of communication, such as voice control, to enter data, e.g., in the form of a questionnaire. Patient interface station 106 may provide the data raw or in processed form to automated diagnostic and treatment system 102, e.g., via a secure communication.

In embodiments, the patient may be prompted, e.g., by a software application, to answer questions intended to aid in the diagnosis of one or more medical conditions. The software application may provide guidance by describing how to use medical instrument equipment 108 to administer a diagnostic test or how to make diagnostic measurements for any particular device that may be part of medical instrument equipment 108 so as to facilitate accurate measurements of patient diagnostic data.

In embodiments, the patient may use medical instrument equipment 108 to create a patient health profile that serves as a baseline profile. Gathered patient-related data may be securely stored in database 103 or a secure remote server (not shown) coupled to automated diagnostic and treatment system 102. In embodiments, automated diagnostic and treatment system 102, supported by and deep learning system 105, enables interaction between a patient and a remotely located health care professional, who may provide instructions to the patient, e.g., by communicating via the software application. A doctor may log into a cloud-based system (not shown) to access patient-related data via doctor interface station 104. The doctor interface station 104 comprises a doctor interface communication module 130. In embodiments, automated diagnostic and treatment system 102 presents automated diagnostic suggestions to a doctor, who may verify or modify the suggested information. Automated diagnostic and treatment system 102 is coupled to doctor interface station 104. Automated diagnostic and treatment system 102 may communicate to doctor interface station 104 alerts, if needed, risk profile, and data integrity 120.

In embodiments, based on one more patient questionnaires, data gathered by medical instrument equipment 108, patient feedback, and historic diagnostic information, the patient may be provided with instructions, feedback, results 122, and other information pertinent to the patient's health. In embodiments, the doctor may select an illness based on automated diagnostic system suggestions and/or follow a sequence of instructions, feedback, and/or results 122 may be adjusted based on decision vectors associated with a medical database. In embodiments, medical instrument equipment 108 uses the decision vectors to generate a diagnostic result, e.g., in response to patient answers and/or measurements of the patient's vital signs.

In embodiments, medical instrument equipment 108 comprises a number of sensors, such as accelerometers, gyroscopes, pressure sensors, cameras, bolometers, altimeters, IR LEDs, and proximity sensors that may be coupled to one or more medical devices, e.g., a thermometer, to assist in performing diagnostic measurements and/or monitor a patient's use of medical instrument equipment 108 for accuracy. A camera, bolometer, or other spectrum imaging device (e.g. radar), in addition to taking pictures of the patient, may use image or facial recognition software and machine vision to recognize body parts, items, and actions to aid the patient in locating suitable positions for taking a measurement on the patient's body, e.g., by identifying any part of the patient's body as a reference.

Examples of the types of diagnostic data that medical instrument equipment 108 may generate comprise body temperature, blood pressure, images, sound, heart rate, blood oxygen level, motion, ultrasound, pressure or gas analysis, continuous positive airway pressure, electrocardiogram, electroencephalogram, electrocardiography, BMI, muscle mass, blood, urine, and any other patient-related data 128. In embodiments, patient-related data 128 may be derived from a non-surgical wearable or implantable monitoring device that gathers sample data.

In embodiments, an IR LED, proximity beacon, or other identifiable marker (not shown) may be attached to medical instrument equipment 108 to track the position and placement of medical instrument equipment 108. In embodiments, a camera, bolometer, or other spectrum imaging device uses the identifiable marker as a control tool to aid the camera or the patient in determining the position of medical instrument equipment 108.

In embodiments, a deep learning system 105, which may include machine vision software, may be used to track and overlay or superimpose, e.g., on a screen, the position of the identifiable marker e.g., IR LED, heat source, or reflective material with a desired target location at which the patient should place medical instrument equipment 108, thereby, aiding the patient to properly place or align a sensor and ensure accurate and reliable readings. Once medical instrument equipment 108, e.g., a stethoscope is placed at the desired target location on a patient's torso, the patient may be prompted by optical, haptic or visual cues to breath according to instructions or perform other actions to facilitate medical measurements and to start a measurement.

In embodiments, one or more sensors that may be attached to medical instrument equipment 108 monitor the placement and usage of medical instrument equipment 108 by periodically or continuously recording data and comparing measured data, such as location, movement, rotation and angles, to an expected data model and/or an error threshold to ensure measurement accuracy. A patient may be instructed to adjust an angle, location, rotation or motion of medical instrument equipment 108, e.g., to adjust its state and, thus, avoid low-accuracy or faulty measurement readings. In embodiments, sensors attached or tracking medical instrument equipment 108 may generate sensor data and patient interaction activity data that may be compared, for example, against an idealized patient medical instrument equipment usage sensor model data to create an equipment usage accuracy score. The patient medical instrument equipment measured medical data may also be compared with idealized device measurement data expected from medical instrument equipment 108 to create a device accuracy score. Recording bioelectric signals may include, for example, but without limitations, electroencephalography, electrocardiography, electrooculography, electromyography and electrogastrography.

Feedback from medical instrument equipment 108 (e.g., sensors, proximity, camera, etc.) and actual device measurement data may be used to instruct the patient to properly align medical instrument equipment 108 during a measurement. In embodiments, medical instrument equipment type and sensor system monitoring of medical instrument equipment 108 patient interaction may be used to create a device usage accuracy score for use in a medical diagnosis algorithm. Similarly, patient medical instrument equipment measured medical data may be used to create a measurement accuracy score for use by the medical diagnostic algorithm. In embodiments, medical instrument equipment 108 may also be fitted with haptic/tactile feedback sensors which may augment audio or screen-based guidance instructions for taking measurement. These haptic feedback devices may include, but are not limited to, vibration motors (similar to those found in smart phones) fitted around the medical instrument equipment to give tactile instructions (e.g. vibration on the left side of the medical device to instruct the patient to move the medical device left), or flywheels to give kinesthetic feedback such as resisting movement in undesirable directions, and aiding movement in the correct direction (similar to certain virtual reality peripherals).

In embodiments, deep learning system 105, which may include machine vision software, may be used to show on a display an animation that mimics a patient's movements and provides detailed interactive instructions and real-time feedback to the patient. This aids the patient in correctly positioning and operating medical instrument equipment 108 relative to the patient's body so as to ensure a high level of accuracy when using medical instrument equipment 108 is operated. In embodiments, the display may be a traditional computer screen. In other embodiments, the display may be augmented/virtual/mixed reality hardware, where patients may interact with the kiosk in a completely virtual environment while wearing AR/VR goggles.

In embodiments, once automated diagnostic and treatment system 102 detects unexpected data, e.g., data representing an unwanted movement, location, measurement data, etc., a validation process comprising a calculation of a trustworthiness score or reliability factor is initiated in order to gauge the measurement accuracy. Once the accuracy of the measured data falls below a desired level, the patient may be asked to either repeat a measurement or request assistance by an assistant, who may answer questions, e.g., remotely via an application to help with proper equipment usage, or alert a nearby person to assist with using medical instrument equipment 108. The validation process, may also instruct a patient to answer additional questions, and may comprise calculating the measurement accuracy score based on a measurement or re-measurement.

In embodiments, upon request 124, automated diagnostic and treatment system 102 may enable a patient-doctor interaction by granting the patient and doctor access to diagnostic system 100. The patient may enter data, take measurements, and submit images and audio files or any other information to the application or web portal. The doctor may access that information, for example, to review a diagnosis generated by automated diagnostic and treatment system 102, and generate, confirm, or modify instructions for the patient. Patient-doctor interaction, while not required for diagnostic and treatment, if used, may occur in person, real-time via an audio/video application, or by any other means of communication.

In embodiments, automated diagnostic and treatment system 102 may utilize images generated from a diagnostic examination of mouth, throat, eyes, ears, skin, extremities, surface abnormalities, internal imaging sources, and other suitable images and/or audio data generated from diagnostic examination of heart, lungs, abdomen, chest, joint motion, voice, and any other audio data sources. Automated diagnostic and treatment system 102 may further utilize patient lab tests, medical images, or any other medical data. In embodiments, automated diagnostic and treatment system 102 enables medical examination of the patient, for example, using medical devices, e.g., ultrasound, in medical instrument equipment 108 to detect sprains, contusions, or fractures, and automatically provide diagnostic recommendations regarding a medical condition of the patient. One skilled in the art may recognize that other methods and systems may be utilized to enable medical examinations of the patient.

In embodiments, diagnosis comprises the use of medical database decision vectors that are at least partially based on the patient's self-measured (or assistant-measured) vitals or other measured medical data, the accuracy score of a measurement dataset, a usage accuracy score of a sensor attached to medical instrument equipment 108, a regional illness trend, and information used in generally accepted medical knowledge evaluations steps. The decision vectors and associated algorithms, which may be installed in automated diagnostic and treatment system 102, may utilize one or more-dimensional data, patient history, patient questionnaire feedback, and pattern recognition or pattern matching for classification using images and audio data. In embodiments, a medical device usage accuracy score generator (not shown) may be implemented within automated diagnostic and treatment system 102 and may utilize an error vector of any device in medical instrument equipment or attached medical instrument equipment 108 to create the device usage accuracy score and utilize the actual patient-measured device data to create the measurement data accuracy score.

In embodiments, automated diagnostic and treatment system 102 outputs diagnosis and/or treatment information that may be communicated to the patient, for example, electronically or in person by a medical professional, e.g., a treatment guideline that may include a prescription for a medication.

In embodiments, prescriptions may be communicated directly to a pharmacy for pick-up or automated home delivery.

In embodiments, automated diagnostic and treatment system 102 may generate an overall health risk profile of the patient and recommend steps to reduce the risk of overlooking potentially dangerous conditions or guide the patient to a nearby facility that can treat the potentially dangerous condition. The health risk profile may assist a treating doctor in fulfilling duties to the patient, for example, to carefully review and evaluate the patient and, if deemed necessary, refer the patient to a specialist, initiate further testing, etc. The health risk profile advantageously reduces the potential for negligence and, thus, medical malpractice.

Automated diagnostic and treatment system 102, in embodiments, comprises a payment feature that uses patient identification information to access a database to, e.g., determine whether a patient has previously arranged a method of payment, and if the database does not indicate a previously arranged method of payment, automated diagnostic and treatment system 102 may prompt the patient to enter payment information, such as insurance, bank, or credit card information. Automated diagnostic and treatment system 102 may determine whether payment information is valid and automatically obtain an authorization from the insurance, EHR system, and/or the card issuer for payment for a certain amount for services rendered by the doctor. An invoice may be electronically presented to the patient, e.g., upon completion of a consultation, such that the patient can authorize payment of the invoice, e.g., via an electronic signature.

In embodiments, database 103 of patient's information (e.g., a secured cloud-based database) may comprise a security interface (not shown) that allows secure access to a patient database, for example, by using patient identification information to obtain the patient's medical history. The interface may utilize biometric, bar code, or other electronically security methods. In embodiments, medical instrument equipment 108 uses unique identifiers that are used as a control tool for measurement data. Database 103 may be a repository for any type of data created, modified, or received by diagnostic system 100, such as generated diagnostic information, information received from patient's wearable electronic devices, remote video/audio data and instructions, e.g., instructions received from a remote location or from the application.

In embodiments, fields in the patient's electronic health care record (EHR) are automatically populated based on one or more of questions asked by diagnostic system 100, measurements taken by the diagnostic system 100, diagnosis and treatment codes generated by diagnostic system 100, one or more trust scores, and imported patient health care data from one or more sources, such as an existing health care database. It is understood the format of imported patient health care data may be converted to be compatible with the EHR format of diagnostic system 100. Conversely, exported patient health care data may be converted, e.g., to be compatible with an external EHR database.

In addition, patient-related data documented by diagnostic system 100 provide support for the code decision for the level of exam a doctor performs. Currently, for billing and reimbursement purposes, doctors have to choose one of any identified codes (e.g., ICD10 currently holds approximately 97,000 medical codes) to identify an illness and provide an additional code that identifies the level of physical exam/diagnosis performed on the patient (e.g., full body physical exam) based on an illness identified by the doctor.

In embodiments, patient answers are used to suggest to the doctor a level of exam that is supported by the identified illness, e.g., to ensure that the doctor does not perform unnecessary in-depth exams for minor illnesses or a treatment that may not be covered by the patient's insurance.

In embodiments, upon identifying a diagnostic system 100 generates one or more recommendations/suggestions/options for a particular treatment. In embodiments, one or more treatment plans are generated that the doctor may discuss with the patient and decide on a suitable treatment. For example, one treatment plan may be tailored purely for effectiveness, another one may consider the cost of drugs. In embodiments, diagnostic system 100 may generate a prescription or lab test request and consider factors, such as recent research results, available drugs and possible drug interactions, the patient's medical history, traits of the patient, family history, and any other factors that may affect treatment when providing treatment information. In embodiments, diagnosis and treatment databases may be continuously updated, e.g., by health care professionals, so that an optimal treatment may be administered to a particular patient, e.g., a patient identified as member of a certain risk group.

It is noted that sensors and measurement techniques may be advantageously combined to perform multiple functions using a reduced number of sensors. For example, an optical sensor may be used as a thermal sensor by utilizing IR technology to measure body temperature. It is further noted that some or all data collected by diagnostic system 100 may be processed and analyzed directly within automated diagnostic and treatment system 102 or transmitted to an external reading device (not shown in FIG. 1) for further processing and analysis, e.g., to enable additional diagnostics.

Figure 2:
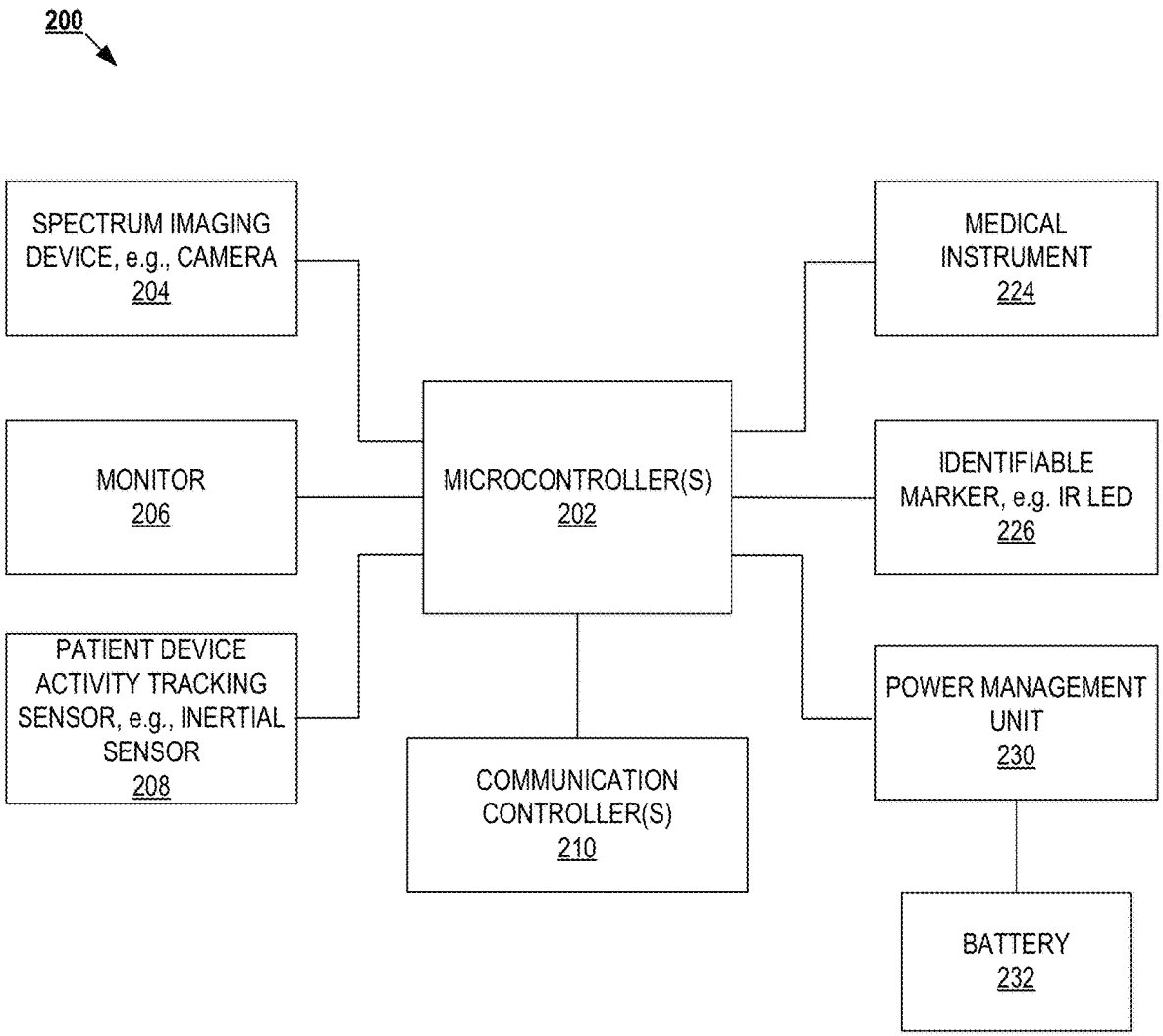
FIG. 2 illustrates an exemplary medical instrument equipment system according to embodiments of the present disclosure.

FIG. 2 illustrates an exemplary patient diagnostic measurement system according to embodiments of the present disclosure. As depicted, patient diagnostic measurement system 200 comprises microcontroller 202, spectrum imaging device, e.g., spectrum imaging device camera 204, monitor 206, patient-medical equipment activity tracking sensors, e.g., inertial sensor 208, communications controller 210, medical instruments 224, identifiable marker, e.g., identifiable marker IR LED 226, power management unit 230, and battery 232. Each component may be coupled directly or indirectly by electrical wiring, wirelessly, or optically to any other component in patient diagnostic measurement system 200. Inertial sensor 208 may also be referred to as patient-equipment activity sensors inertial sensors 208 or simply sensors 208.

Medical instrument 224 comprises one or more devices that are capable of measuring physical and non-physical characteristics of a patient that, in embodiments, may be customized, e.g., according to varying anatomies among patients, irregularities on a patient's skin, and the like. In embodiments, medical instrument 224 is a combination of diagnostic medical devices that generate diagnostic data based on patient characteristics. Exemplary diagnostic medical devices are heart rate sensors, otoscopes, digital stethoscopes, in-ear thermometers, blood oxygen sensors, high-definition cameras, spirometers, blood pressure meters, respiration sensors, skin resistance sensors, glucometers, ultrasound devices, electrocardiographic sensors, body fluid sample collectors, eye slit lamps, weight scales, and any devices known in the art that may aid in performing a medical diagnosis. In embodiments, patient characteristics and vital signs data may be received from and/or compared against wearable or implantable monitoring devices that gather sample data, e.g., a fitness device that monitors physical activity.

One or more medical instruments 224 may be removably attachable directly to a patient's body, e.g., torso, via patches or electrodes that may use adhesion to provide good physical or electrical contact. In embodiments, medical instruments 224, e.g., a contact-less (or non-contact) thermometer, may perform contact-less measurements some distance away from the patient's body. Contact, and non-contact sensors may also support measurements for any number of bioelectric recordings, including but not limited to, electrocardiogram (ECG), electroencephalogram (EEG), electromyogram (EMG), electrooculogram (EOG), and electrogastrogram (EGG).

In embodiments, microcontroller 202 may be a secure microcontroller that securely communicates information in encrypted form to ensure privacy and the authenticity of measured data and activity sensor and patient-equipment proximity information and other information in patient diagnostic measurement system 200. This may be accomplished by taking advantage of security features embedded in hardware of microcontroller 202 and/or software that enables security features during transit and storage of sensitive data. Each device in patient diagnostic measurement system 200 may have keys that handshake to perform authentication operations on a regular basis.

Spectrum imaging device camera 204 is any audio/video device that may capture patient images and sound at any frequency or image type. Monitor 206 is any screen or display device that may be coupled to camera, sensors and/or any part of patient diagnostic measurement system 200. Patient-equipment activity tracking inertial sensor 208 is any single or multi-dimensional sensor, such as an accelerometer, a multi-axis gyroscope, pressure sensor, and a magnetometer capable of providing position, motion, pressure on medical equipment or orientation data based on patient interaction. Patient-equipment activity tracking inertial sensor 208 may be attached to (removably or permanently) or embedded into medical instrument 224. Identifiable marker IR LED 226 represents any device, heat source, reflective material, proximity beacon, altimeter, etc., that may be used by microcontroller 202 as an identifiable marker. Like patient-equipment activity tracking inertial sensor 208, identifiable marker IR LED 226 may be attachable to or embedded into medical instrument 224.

In embodiments, communication controller 210 is a wireless communications controller attached either permanently or temporarily to medical instrument 224 or the patient's body to establish a bi-directional wireless communications link and transmit data, e.g., between sensors and microcontroller 202 using any wireless communication protocol known in the art, such as Bluetooth Low Energy, e.g., via an embedded antenna circuit that wirelessly communicates the data. One of ordinary skill in the art will appreciate that electromagnetic fields generated by such antenna circuit may be of any suitable type. In case of an RF field, the operating frequency may be located in the ISM frequency band, e.g., 13.56 MHz. In embodiments, data received by communications controller 210 may be forwarded to a host device (not shown) that may run a software application.

In embodiments, power management unit 230 is coupled to microcontroller 202 to provide energy to, e.g., microcontroller 202 and communication controller 210. Battery 232 may be a back-up battery for power management unit 230 or a battery in any one of the devices in patient diagnostic measurement system 200. One of ordinary skill in the art will appreciate that one or more devices in patient diagnostic measurement system 200 may be operated from the same power source (e.g., battery 232) and perform more than one function at the same or different times. A person of skill in the art will also appreciate that one or more components, e.g., sensors 208, identifiable marker IR LED 226, may be integrated on a single chip/system, and that additional electronics, such as filtering elements, etc., may be implemented to support the functions of medical instrument equipment measurement or usage monitoring and tracking in patient diagnostic measurement system 200 according to the objectives of the invention.

In operation, a patient may use medical instrument 224 to gather patient data based on physical and non-physical patient characteristics, e.g., vital signs data, images, sounds, and other information useful in the monitoring and diagnosis of a health-related condition. The patient data is processed by microcontroller 202 and may be stored in a database (not shown). In embodiments, the patient data may be used to establish baseline data for a patient health profile against which subsequent patient data may be compared.

In embodiments, patient data may be used to create, modify, or update EHR data. Gathered medical instrument equipment data, along with any other patient and sensor data, may be processed directly by patient diagnostic measurement system 200 or communicated to a remote location for analysis, e.g., to diagnose existing and expected health conditions to benefit from early detection and prevention of acute conditions or aid in the development of novel medical diagnostic methods.

In embodiments, medical instrument 224 is coupled to a number of sensors, such as patient-equipment tracking inertial sensor 208 and/or identifiable marker IR LED 226, that may monitor a position/orientation of medical instrument 224 relative to the patient's body when a medical equipment measurement is taken. In embodiments, sensor data generated by sensor 208, identifiable marker IR LED 226 or other sensors may be used in connection with, e.g., data generated by spectrum imaging device camera 204, proximity sensors, transmitters, bolometers, or receivers to provide feedback to the patient to aid the patient in properly aligning medical instrument 224 relative to the patient's body part of interest when performing a diagnostic measurement. A person skilled in the art will appreciate that not all sensors 208, identifiable marker IR LED 226, beacon, pressure, altimeter, etc., need to operate at all times. Any number of sensors may be partially or completely disabled, e.g., to conserve energy.

In embodiments, the sensor emitter comprises a light signal emitted by IR LED 226 or any other identifiable marker that may be used as a reference signal. In embodiments, the reference signal may be used to identify a location, e.g., within an image and based on a characteristic that distinguishes the reference from other parts of the image. In embodiments, the reference signal is representative of a difference between the position of medical instrument 224 and a preferred location relative to a patient's body. In embodiments, spectrum imaging device camera 204 displays, e.g., via monitor 206, the position of medical instrument 224 and the reference signal at the preferred location so as to allow the patient to determine the position of medical instrument 224 and adjust the position relative to the preferred location, displayed by spectrum imaging device camera 204.

Spectrum imaging device camera 204, proximity sensor, transmitter, receiver, bolometer, or any other suitable device may be used to locate or track the reference signal, e.g., within the image, relative to a body part of the patient. In embodiments, this augmented reality (AR) method may be accomplished by using an overlay method that overlays an image of a body part of the patient against an ideal model of device usage to enable real-time feedback for the patient. The reference signal along with signals from other sensors, e.g., patient-equipment activity inertial sensor 208, may be used to identify a position, location, angle, orientation, or usage associated with medical instrument 224 to monitor and guide a patient's placement of medical instrument 224 at a target location and accurately activate a device for measurement. In other embodiments, methods of mixed reality, in which users wearing AR goggles may have virtual objects overlaid on real-world objects (e.g. a virtual clock on a real wall).

In embodiments, e.g., upon receipt of a request signal, microcontroller 202 activates one or more medical instruments 224 to perform measurements and sends data related to the measurement back to microcontroller 202. The measured data and other data associated with a physical condition may be automatically recorded and a usage accuracy of medical instrument 224 may be monitored.

In embodiments, microcontroller 202 uses an image in any spectrum, motion signal and/or an orientation signal by patient-equipment activity inertial sensor 208 to compensate or correct the vital signs data output by medical instrument 224. Data compensation or correction may comprise filtering out certain data as likely being corrupted by parasitic effects and erroneous readings that result from medical instrument 224 being exposed to unwanted movements caused by perturbations or, e.g., the effect of movements of the patient's target measurement body part.

In embodiments, signals from two or more medical instruments 224, or from medical instrument 224 and patient-activity activity system inertial sensor 208, are combined, for example, to reduce signal latency and increase correlation between signals to further improve the ability of patient diagnostic measurement system 200 to reject motion artifacts to remove false readings and, therefore, enable a more accurate interpretation of the measured vital signs data.

In embodiments, spectrum imaging device camera 204 and medical instrument monitor 206 displays actual or simulated images and videos of the patient and medical instrument 224 to assist the patient in locating a desired position for medical instrument 224 when performing the measurement so as to increase measurement accuracy. Spectrum imaging device camera 204 may use image or facial recognition software to identify and display eyes, mouth, nose, ears, torso, or any other part of the patient's body as reference.

In embodiments, patient diagnostic measurement system 200 uses machine vision software that analyzes measured image data and compares image features to features in a database, e.g., to detect an incomplete image for a target body part, to monitor the accuracy of a measurement and determine a corresponding score. In embodiments, if the score falls below a certain threshold, patient diagnostic measurement system 200 may provide detailed guidance for improving measurement accuracy or to receive a more complete image, e.g., by providing instructions on how to change an angle or depth of an otoscope relative to the patient's ear.

In embodiments, the deep learning system may use an overlay method to mimic a patient's posture/movements to provide detailed and interactive instructions, e.g., by displaying a character, image of the patient, graphic, or avatar on monitor 206 to provide feedback to the patient. The instructions, image, or avatar may start or stop and decide what help instruction to display based on the type of medical instrument 224, the data from spectrum imaging device camera 204, patient-equipment activity sensors inertial sensors 208, bolometer, transmitter and receiver, and/or identifiable marker IR LED 226 (an image, a measured position or angle, etc.), and a comparison of the data to idealized data. This further aids the patient in correctly positioning and operating medical instrument 224 relative to the patient's body, ensures a high level of accuracy when operating medical instrument 224, and solves potential issues that the patient may encounter when using medical instrument 224.

In embodiments, instructions may be provided via monitor 206 and describe in audio/visual format and in any desired level of detail, how to use medical instrument 224 to perform a diagnostic test or measurement, e.g., how to take temperature, so as to enable patients to perform measurements of clinical-grade accuracy. In embodiments, each sensor 208, identifiable marker IR LED 226, e.g., proximity, bolometer, transmitter/receiver may be associated with a device usage accuracy score. A device usage accuracy score generator (not shown), which may be implemented in microcontroller 202, may use the sensor data to generate a medical instrument usage accuracy score that is representative of the reliability of medical instrument 224 measurement on the patient. In embodiments, the score may be based on a difference between an actual position of medical instrument 224 and a preferred position. In addition, the score may be based on detecting a motion, e.g., during a measurement. In embodiments, the device usage accuracy score is derived from an error vector generated for one or more sensors 208, identifiable marker IR LED 226, deep learning system 105. In embodiments, the device usage accuracy score is derived from an error vector generated for one or more sensors 208, identifiable marker IR LED 226. The resulting device usage accuracy score may be used when generating or evaluating medical diagnosis data.

In embodiments, microcontroller 202 analyzes the patient measured medical instrument data to generate a trust score indicative of the acceptable range of the medical instrument. For example, by comparing the medical instrument measurement data against reference measurement data or reference measurement data that would be expected from medical instrument 224. As with device usage accuracy score, the trust score may be used when generating or evaluating a medical diagnosis data.

Figure 3A:
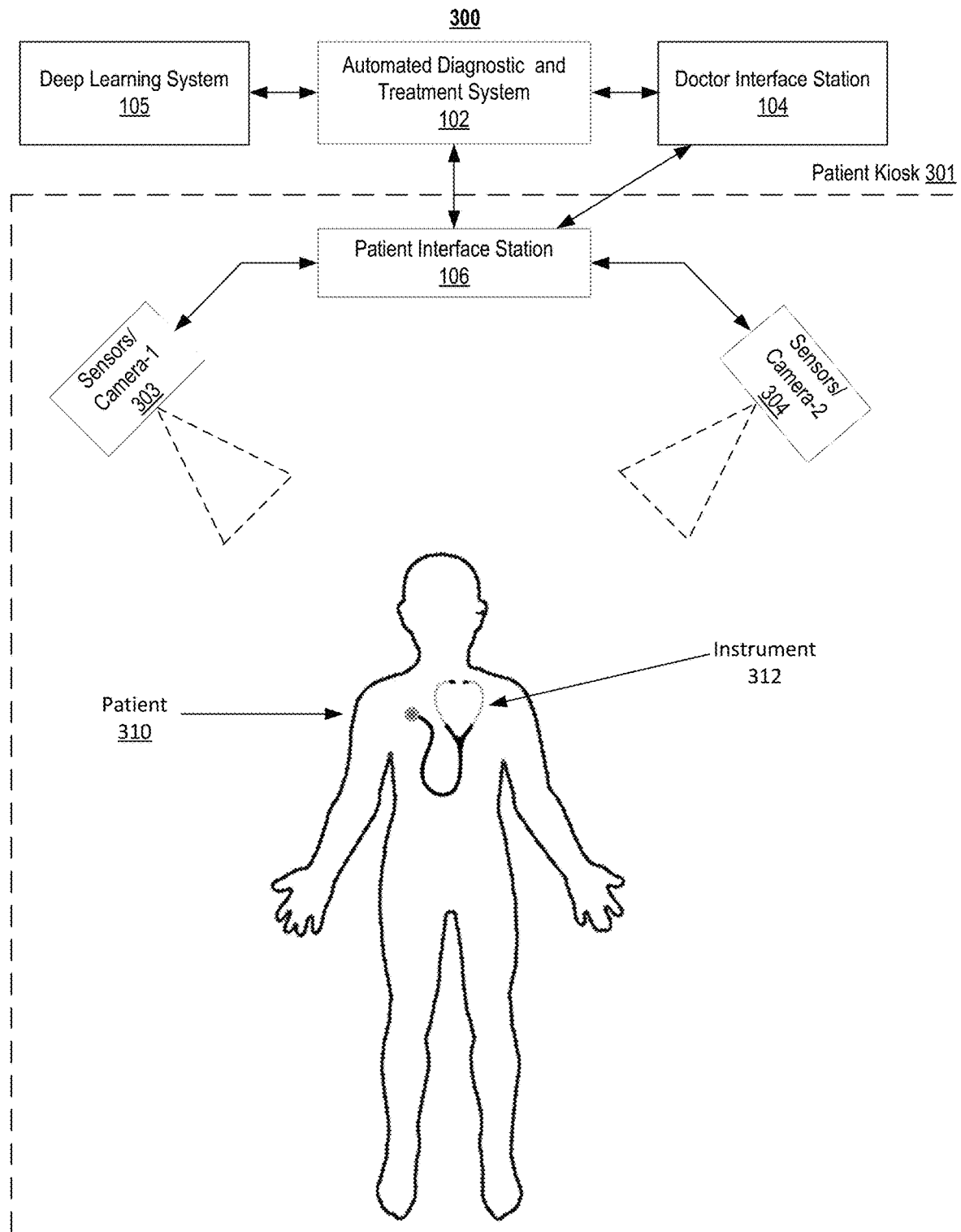
FIG. 3A illustrates an exemplary system for measuring a patient's body parts utilizing audio medical instruments and deep learning systems according to embodiments of the present disclosure.

FIG. 3A illustrates an exemplary system 300 for measuring a patient's body parts utilizing audio medical instruments and deep learning systems according to embodiments of the present disclosure. System 300 may comprise automated diagnostic and treatment system 102, deep learning system 105, doctor interface station 104 and patient kiosk 301. Patient kiosk 301 may comprise patient interface station 106, kiosk cameras including sensors/camera-1 303, sensors/camera-2 304 and instrument 312. As illustrated, patient 310 is present in patient kiosk 301. Kiosk cameras may also be referred to as camera modules. Instrument 312 may be, but not limited to, a stethoscope. Deep learning system 105 may be, but not limited to, a deep convolution neural network (DCNN). System 300 facilities a method of computer vision which may utilize pose estimation and object tracking. A stethoscope may be operable to detect an audio signal of the patient when positioned within an object tracking area of the patient.

An objective of system 300 includes the accurate acquisition of medical measurement data of a target spot of a body part of patient 310. To assist in acquiring accurate medical measurement data, the automated diagnostic and treatment system 102 provides instructions to patient 310 to allow patient 310 to precisely position instrument 312 in proximity to a target spot of a body part of patient 310. That is, the movement of instrument 312 may be controlled by the patient 310. Based on a series of images acquired from the kiosk cameras and instrument 312, these instructions may be generated. Subsequent images from instrument 312 are analyzed by automated diagnostic and treatment system 102 utilizing database 103 and deep learning system 105 to obtain measured medical data. The accuracy of the instrument 312 positioning and the medical measured data may be determined by automated diagnostic and treatment system 102, and deep learning system 105 via an error threshold measurement. When accurately positioned, quality medical measurements are generated for the target spot of a body part of patient 310. As illustrated in FIG. 3A, patient 310 has positioned instrument 312, which may be a stethoscope, in proximity to the heart of patient 310. If the stethoscope is within a recording threshold of the heart of patient 310, a recording may be obtained. The recording threshold may be, but without limitations, less than one inch. In other embodiments, instrument 312 may be positioned within a recording threshold to another body part. In other embodiments, patient 310 may be fitted with haptic/tactile feedback sensors which may augment the patient guidance instructions for taking measurements. These haptic feedback devices, or haptic feedback sensors, may include, but are not limited to, vibration motors (similar to those found in smart phones) fitted around the medical instrument equipment to give tactile instructions (e.g. vibration on the left side of the medical device to instruct the patient to move the medical device left), or flywheels to give kinesthetic feedback such as resisting movement in undesirable directions, and aiding movement in the correct direction (similar to certain virtual reality peripherals). Instrument 312 may be wirelessly coupled to patient interface station 106.

The automated diagnostic and treatment system 102, deep learning system 105, doctor interface station 104 and patient interface station 106 are operable as previously described herein relative to FIG. 1. Collectively, these systems and stations, using pose estimation and object tracking methods, may determine with computer vision if the stethoscope has been moved to the location by patient 310 to allow an audio recording. The automated diagnostic and treatment system 102 may send a command to the patient interface station 106 requesting sensors/camera-1 303 and sensors/camera-2 304 to capture images of patient 310 and instrument 312. The captured images (sometimes called "posed" images) may be analyzed by the deep learning system 105 to determine the position of instrument 312 relative to the body part. From this positioning analysis, the automated diagnostic and treatment system 102 may provide an initial set of instructions to patient 310 to assist patient 310 to position instrument 312 within a pose threshold to the target spot of the body part. After patient 310 acts on the first set of instructions, the deep learning system 105 may captures a second set of images and determines if instrument 312 is within a the pose threshold of the target spot of the body part. The pose threshold may be less than one inch.

As illustrated in patient kiosk 301, there are two camera/sensor modules. In some embodiments, there may be N camera/sensor modules, where N is equal to one of more camera/sensor modules.

A stethoscope examination by the automated diagnostic and treatment system 102 and deep learning system 105 may include the following tasks:

After a pose estimate, using pose estimation and object tracking methods, the deep learning system 105 may determine, with computer vision, if instrument 312 (stethoscope) has been moved to a correct location by the patient 310 for an audio recording. A correct location means the stethoscope is positioned within an object tracking area of the body, or within a recording threshold of a recording site.

Using digital signal processing techniques (DSP), the deep learning system 105 may confirm that the stethoscope has been turned on.

Using DSP techniques, the deep learning system 105 may "clean" the audio signal acquired from stethoscope. This step may be referred to as pre-processing.

Using Machine Learning (ML) techniques, the deep learning system 105 may determine if a Signal of Interest (SoI), in this case, e.g., but without limitations, heart, lung, bowel, muscle, skin or abdomen sounds, are present in the pre-processed audio sample. This step may be referred to as "validation". The ML techniques may be implemented in the automated diagnostic and treatment system 102.

If the SoI is present in the pre-processed audio sample, the deep learning system 105 may use ML techniques to evaluate characteristics in the signal which indicate the presence of abnormalities in the organ being measure, e.g. crackling of lungs. This step may be referred to as "classification" or "symptom classification".

The aforementioned tasks will be further discussed relative to FIGS. 4A, 4B, 4C, 4D, 4E and FIGS. 5A, 5B, 5C.

Figure 3B:
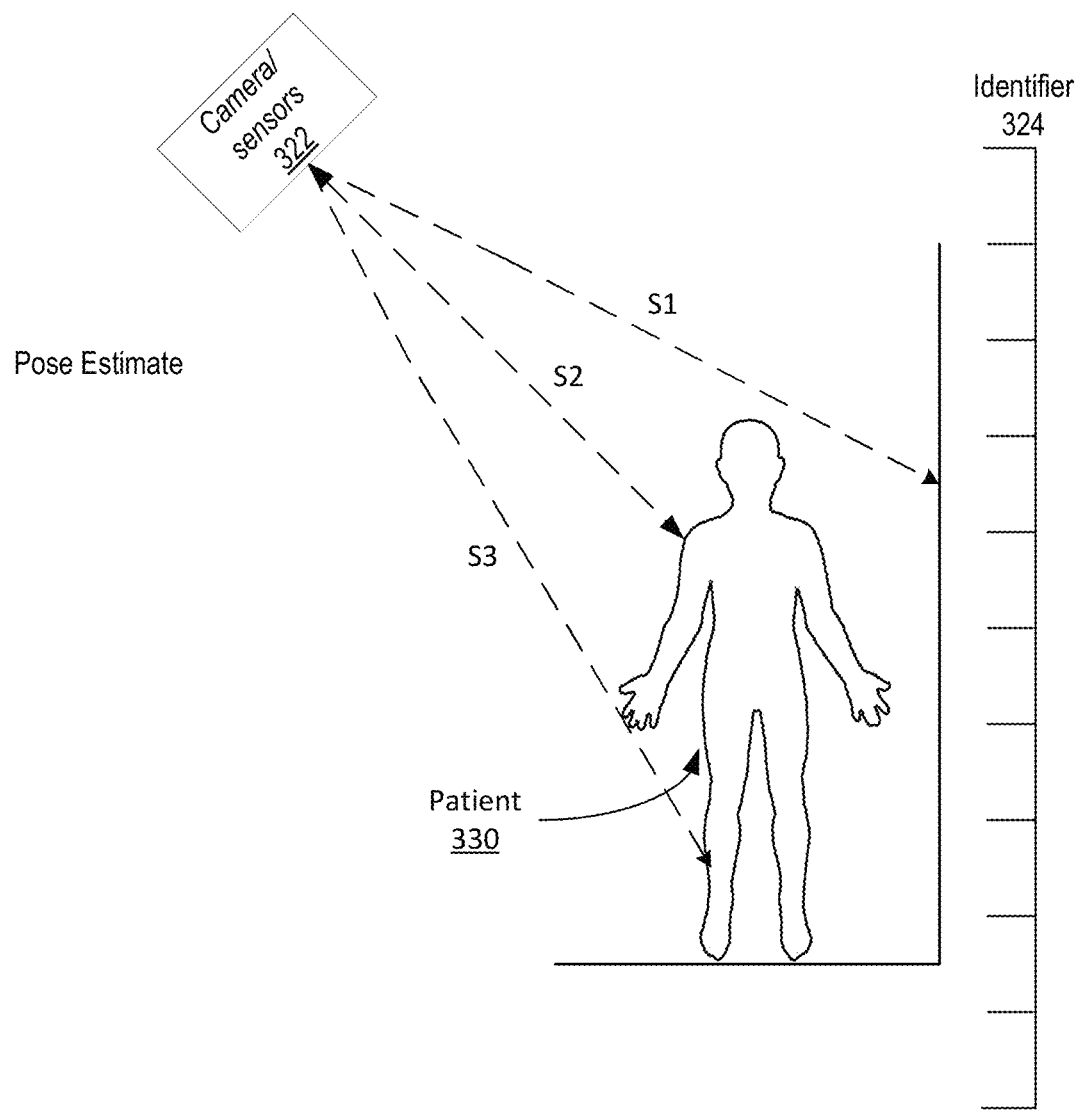
FIG. 3B illustrates another exemplary system for measuring a patient's body parts utilizing cameras and sensors according to embodiments of the present disclosure.

FIG. 3B illustrates another exemplary system 320 for measuring a patient's body parts utilizing cameras and sensors according to embodiments of the present disclosure. System 320 is based on the principle of determine the time-of-flight (TOF) for each emitted pulse of light. Light detection and ranging systems, such as camera/sensors 322, may employ pulses of light to measure distance to an object based on the time of flight (TOF) of each pulse of light. A pulse of light emitted from a light source of a light detection and ranging system interacts with a distal object. A portion of the light reflects from the object and returns to a detector of the light detection and ranging system. Based on the time elapsed between emission of the pulse of light and detection of the returned pulse of light, the distance to the object may be estimated.

The light pulse may hit multiple objects, each having a different distance from the laser, causing multi-return signals to be received by the light detection and ranging system detector. Multi-return signals may provide more information of the environment to improve mapping or reconstruction. A dedicated detector may be required to precisely identify each return with its associated time delay information. The resulting images may be referred to as "pose images". In other words, one or more camera modules may provide a pose estimate based on time of flight of multiple light signals emitted from each of the one or more camera modules and reflected back to the one or more camera modules.

As illustrated in FIG. 3B, camera/sensors 322 may emits signals S1, S2 and S3. These signals may reflect off patient 330 or off a fixed surface, such as a wall or floor. In the kiosk, the walls and floor may have identifiers that can assist in the image identification of the body part of patient 330. The reflection of signals S1, S2 and S3 may be detected by camera/sensors 322 and communicated to a diagnostic system, such as automated diagnostic and treatment system 102. Automated diagnostic and treatment system 102 can determine the distances associated with signals S1, S2 and S3 based on the TOF of each signal. This process may result in a pose estimate, which may be viewed as a pose image. Identifier 324 may assist in identifying a position of a patient's body parts or a medical instrument.

Figure 4B:
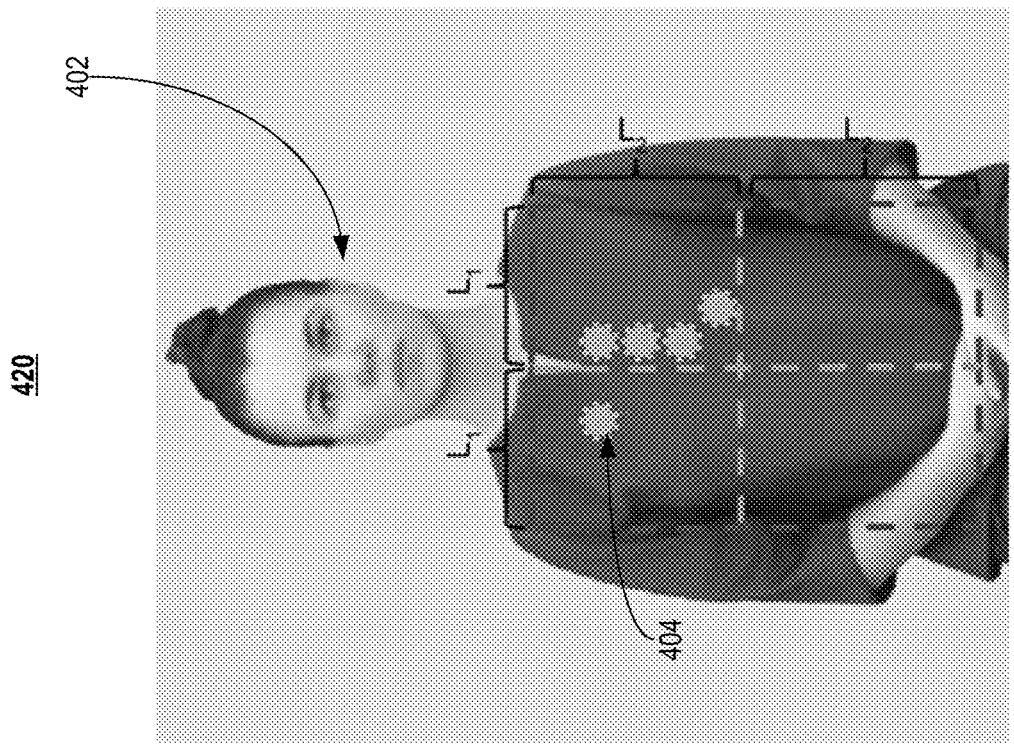
FIGS. 4A, 4B, 4C, and 4D illustrate an exemplary method for identifying a patient's body parts and body recording sites according to embodiments of the present disclosure.
Figure 4A:
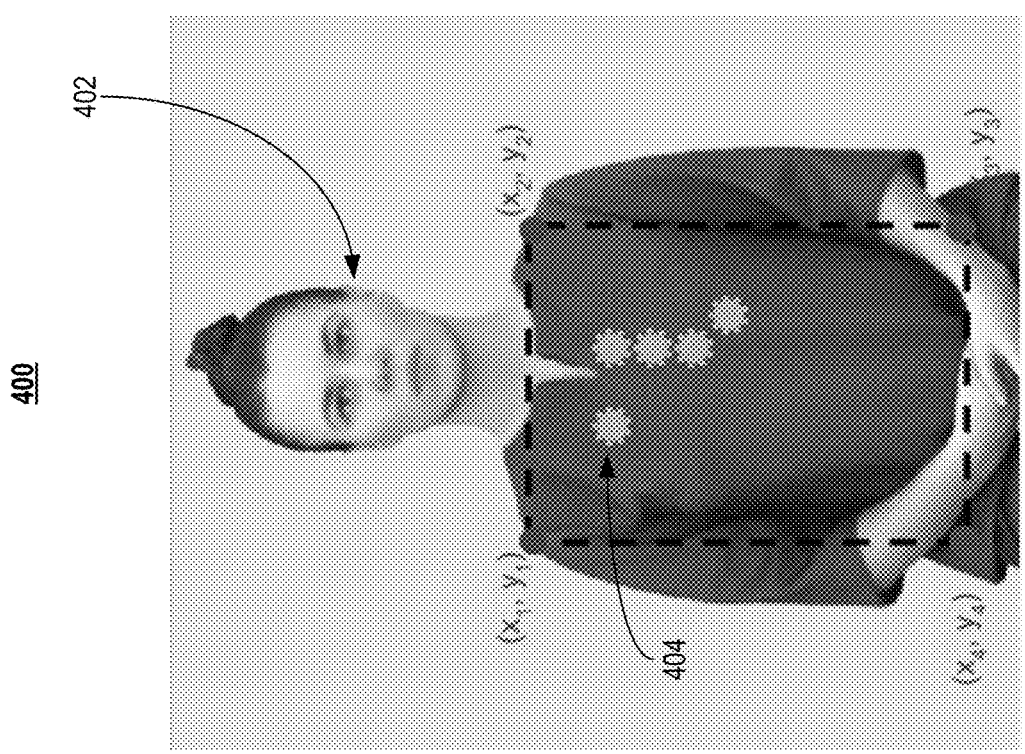
Figure 4D:
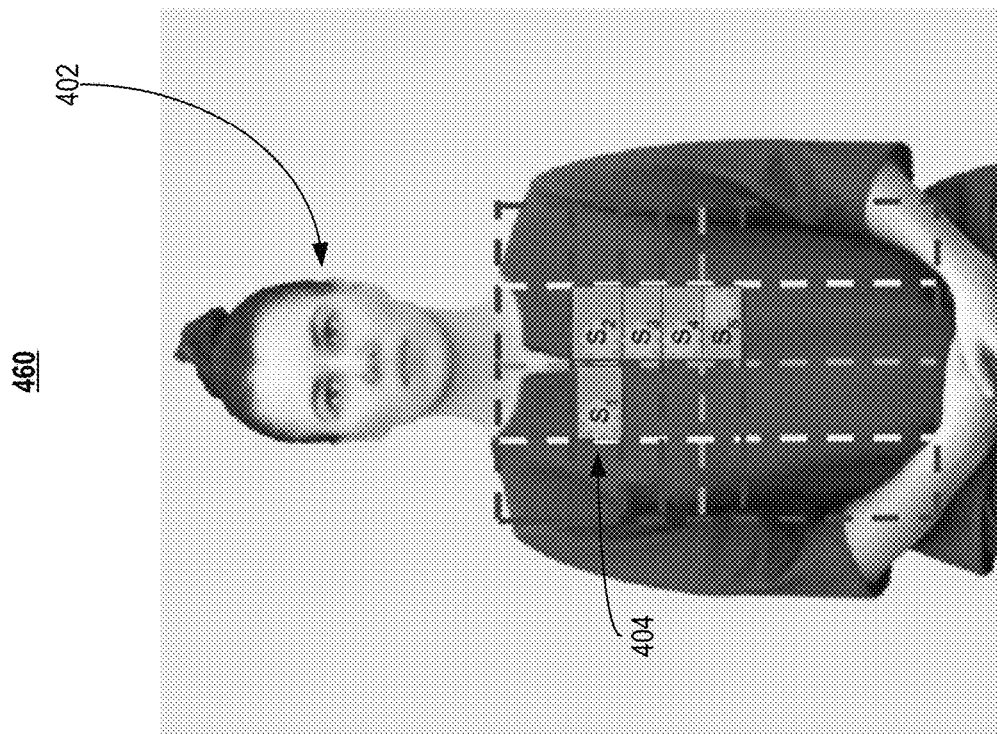
Figure 4C:
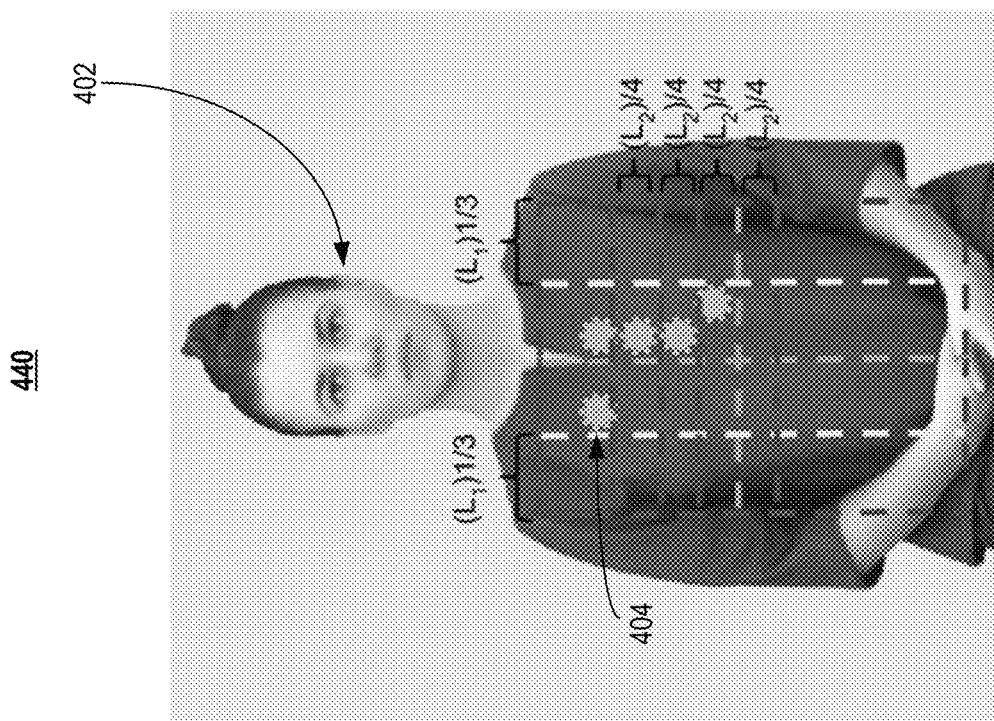

FIGS. 4A, 4B, 4C, and 4D illustrates an exemplary method for identifying a patient's body parts and body recording sites according to embodiments of the present disclosure. FIG. 4A illustrates embodiment 400 of patient 402. To begin, four coordinate points $((x_1, y_1), (x_2, y_2), (x_4, y_4), (x_3, y_3))$ of a bounding box for the body trunk may be estimated utilizing a deep learning algorithm from deep learning system 105, as illustrated in FIG. 4A. Indicator 404 identifies one potential recording site, as noted by the circle, which has an image like a poker chip. Embodiment 400 comprises a total of the five potential recording sites in the bounding box. Next, in embodiment 420 of FIG. 4B, the bounding box may be subdivided into four quadrants. The four quadrants are identified by the intervals of $L_1$ and $L_2$ on FIG. 4B. Then, the four quadrants may be further subdivided into a grid, as illustrated in embodiment 440 of FIG. 4C. In embodiment 440, the grid is based on segments having values of $\frac{1}{3}$ $(L_1)$ and $(L_2)/4$. Embodiment 460 of FIG. 4D may identify certain grid areas corresponding to potential recording sites, $s_1$, $s_2$, $s_3$, $s_4$, and $s_5$. This grid identification process may be supported by patient kiosk 301, automated diagnostic and treatment system 102 and deep learning system 105. One skilled in the art may recognize that other exemplary methods may be utilized for identifying a patient's body parts and body recording sites.

Figure 4E:
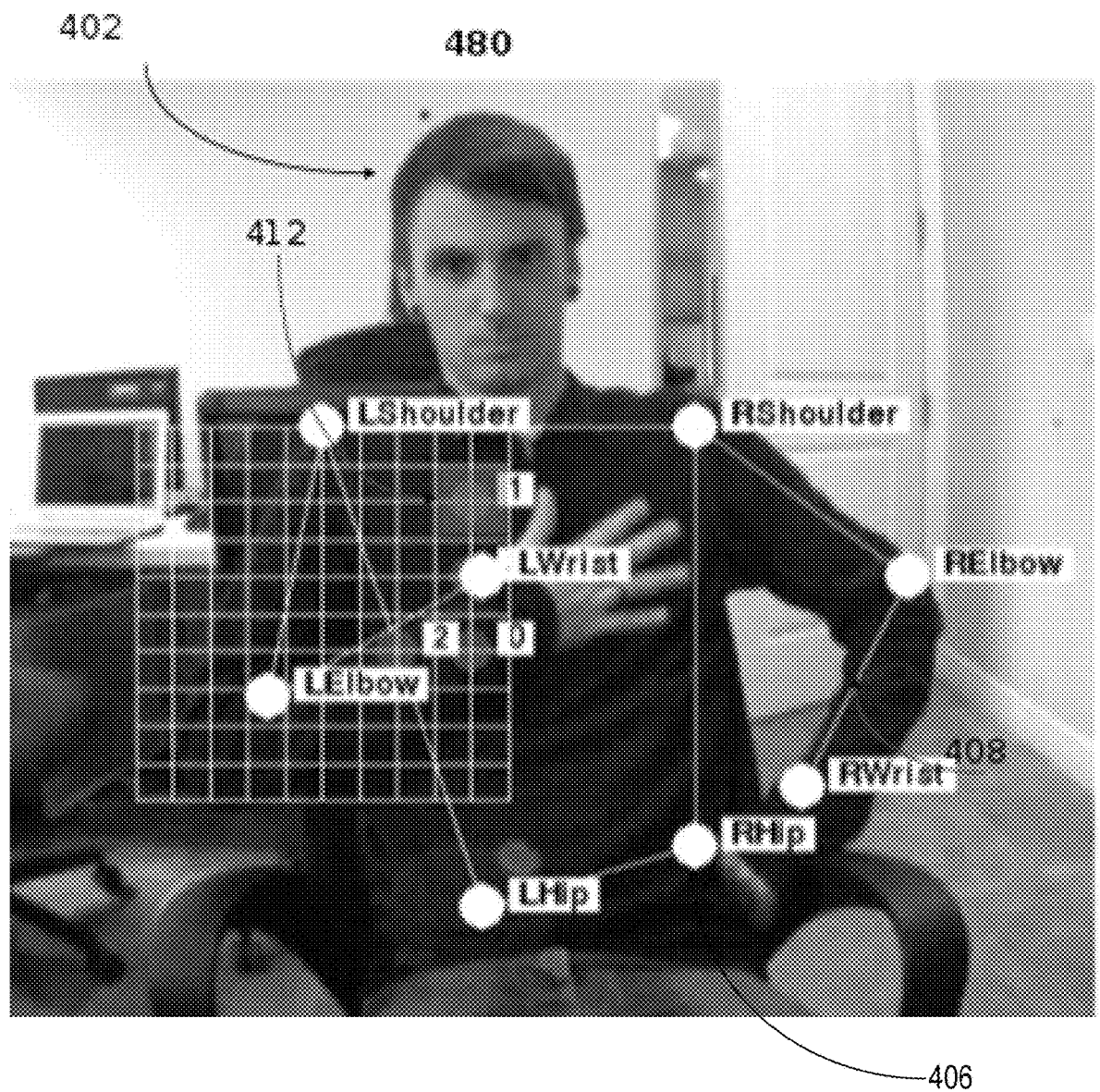
FIG. 4E illustrates exemplary method for the identification of body parts of a patient and the positioning of a stethoscope for recording audio measurement of the body according to embodiments of the present disclosure.

FIG. 4E illustrates an exemplary embodiment 480 for the identification of body parts of patient 402 and the positioning of a stethoscope for recording audio measurement of the body according to embodiments of the present disclosure. More specifically, FIG. 4E illustrates the use of ML and deep learning system 105 to obtain pose estimates of the body parts. With the pose estimates, which are generated via from computer vision, deep learning system 105, joints 406 and limbs 408 may be identified. The white dots on FIG. 4E illustrate the joints including LShoulder, Rshoulder, RElbow, RWrist, RHip, LHip, LElbow and LWrist. The gray dots on FIG. 4E illustrate potential recording sites, as indicated by the numbers 1, 2, 3 and 0. The lines between the white dots illustrate the limbs 408 of the patient 402. Eight joints are identified in FIG. 4E. Using a complementary object tracking deep learning algorithm, the algorithm tracks the identifiable marker (e.g. hand, stethoscope, IR LED) location and determines if the hand is holding the stethoscope has moved into the object tracking area 412. Object tracking area 412 may comprise at least one of the recording sites. When a stethoscope moves within object tracking area 412, a stethoscope may be able to record an audio signal. Effectively, when a stethoscope moves within object tracking area 412, the stethoscope is within a recording threshold of a recording site. One skilled in the art may recognize that other methods and systems may be utilized for the identification of a patient's body parts and stethoscope positioning for recording audio measurements of the body.

In some embodiments, there may be assumptions related to the handling and position of the stethoscope in the hand of patient 402. The assumptions may include: 1) When held, the stethoscope will be occluded by the hand. This means the deep learning system 105 cannot reliable perform object tracking on the stethoscope. 2) The hand which holds the stethoscope may be a viable proxy for the stethoscope location. 3) When tracking the hand holding of the stethoscope, the position of the stethoscope may be estimated with an acceptable level of accuracy. The hand in this case can be referred to as the Identifiable Marker. 4) A sensor board attached to the stethoscope can validate that the stethoscope is in the hand of patient 402 by sending a signal to the automated diagnostic and treatment system 102. 5) The validation that the stethoscope is positioned in the correct location for recording may be based on computer vision and the presence of the signal of interest (SoI) in a stethoscope signal.

Figure 5A:
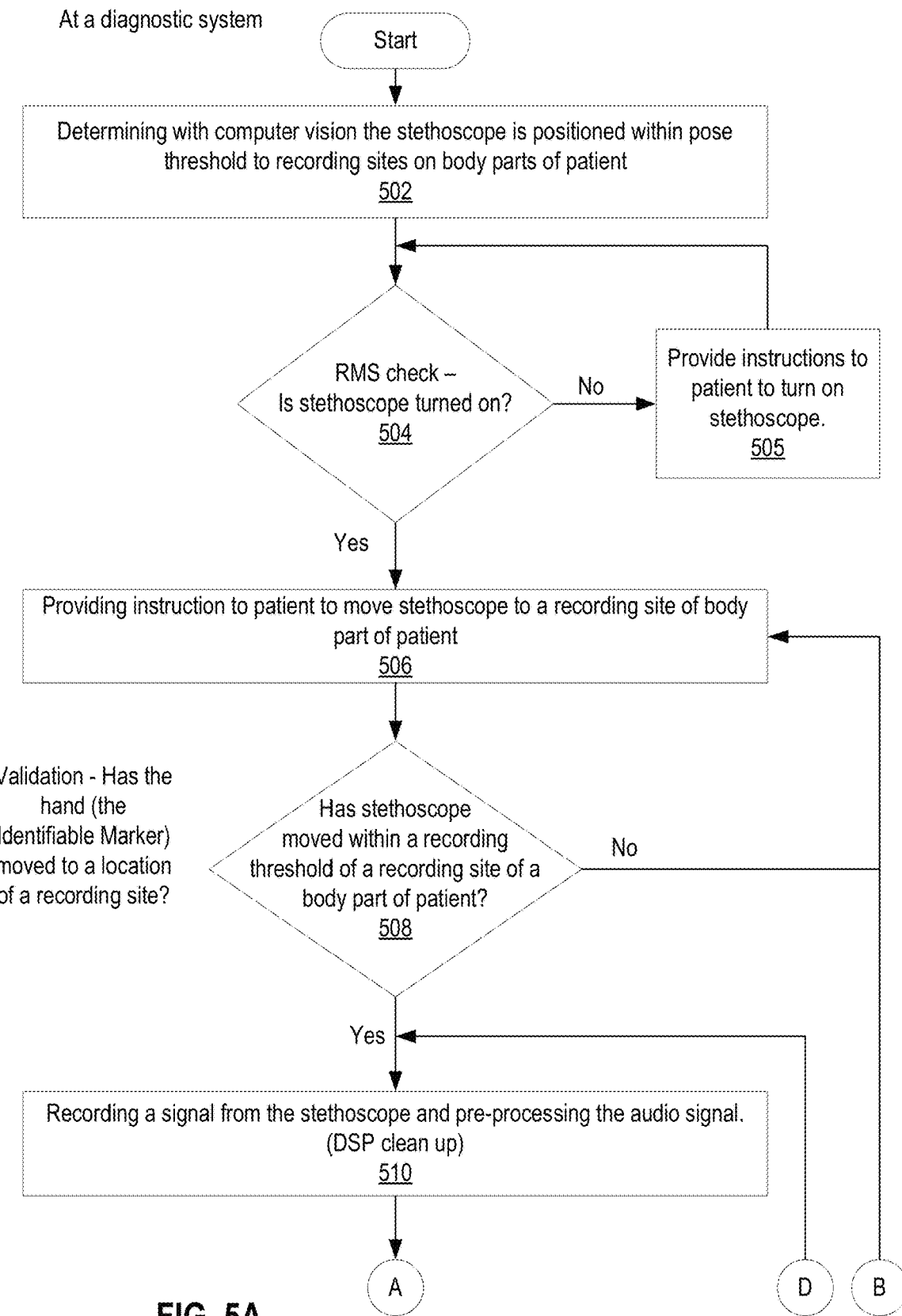
FIGS. 5A and 5B are flowcharts of exemplary methods for making accurate medical instrument patient audio measurements according to embodiments of the present disclosure.
Figure 5B:
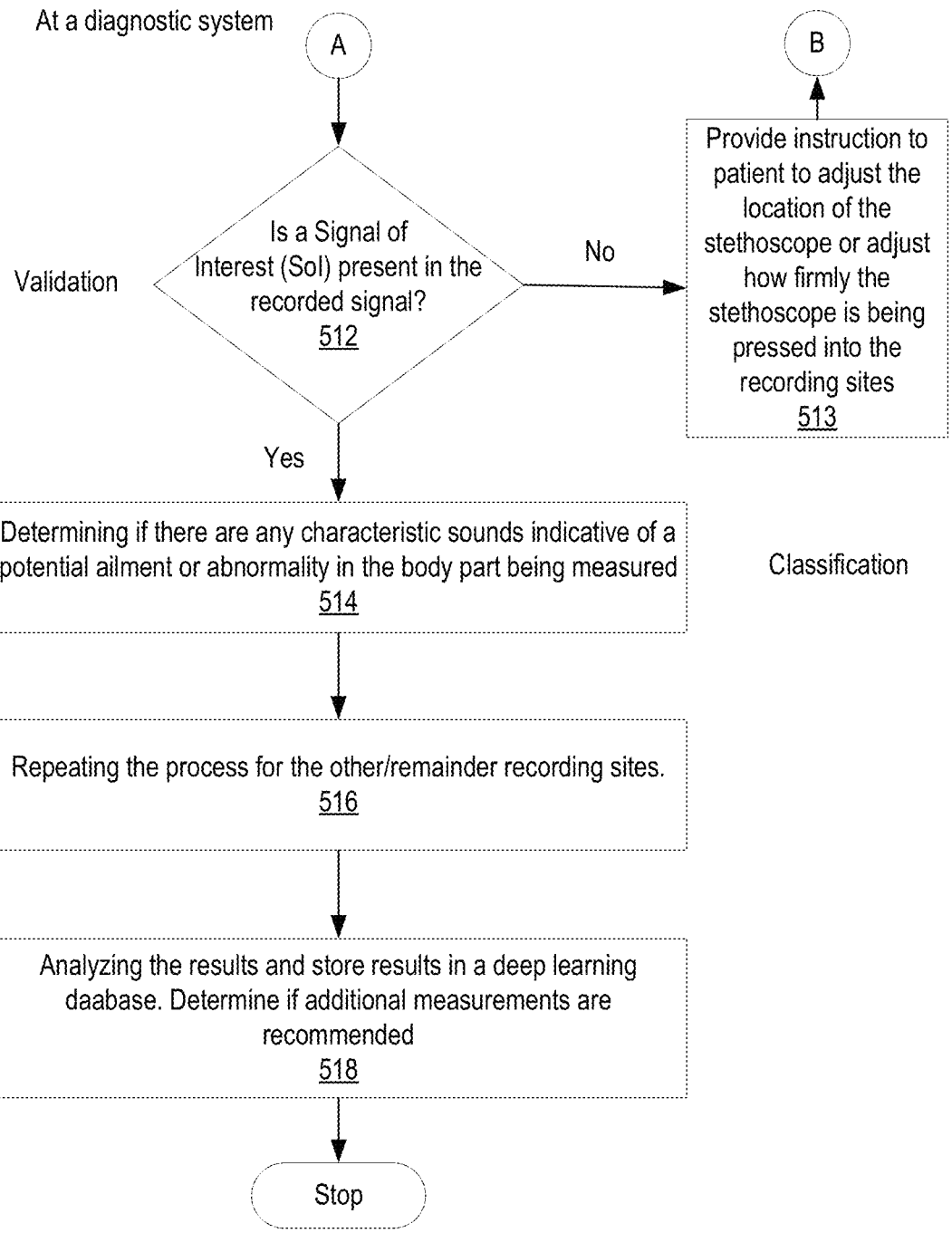

FIGS. 5A and 5B are flowcharts 500 and 540 of exemplary methods for making accurate medical instrument patient audio measurements, according to embodiments of the present disclosure. This method references a stethoscope, but those skilled in the art may recognize that the method may apply to other types of audio instruments. The method may comprise the following steps:

Determining with computer vision the stethoscope is positioned within a pose threshold to recording sites of body parts of the patient 310. Computer vision generates pose estimates from the kiosk cameras. Pose estimation and object tracking methods may identify multiple recording sites on the patient 310. (step 502)

Implementing a RMS check or confidence check. Using digital signal processing techniques (DSP) implemented by the deep learning system 105, confirm whether the stethoscope operating, i.e., is turned on. More specifically, to ensure the user has turned the stethoscope on, DSP techniques may be utilized by the evaluation of the incoming audio signal from the stethoscope by analyzing the Root Mean Square (RMS) of the amplitude of the incoming audio signal. (step 504) If no signal is present (or the RMS value is too low), patient kiosk 301 may instruct the user to turn on the stethoscope, or increase the volume. (step 505), then repeat step 504.

If the stethoscope is turned on, providing, by the automated diagnostic and treatment system 102, instruction to patient 310 to move the stethoscope to a recording site of body part of patient. The instructions provide the user with a set of visual directions and/or haptic/tactile feedback to move the stethoscope into the correct location for the first recording site. Recording sites may be identified by an object tracking area 412 (step 506)

Is stethoscope positioned at a recording site for a body part of patient? If yes, the position of the tracked object (e.g. hand of the patient, or medical device) is validated. Each incoming frame/image from the patient kiosk 301 may be evaluated by the deep learning system 105 to determine if the patient has moved the stethoscope within a recording threshold of a recording site. The recording site may be within an object tracking area, as previously discussed. This determination may be based on the corroborating evidence from the object tracking algorithm identifying the location of the hand at a recording site, pose estimation of the patient, and incoming data from the sensor board attached to the stethoscope. If the stethoscope is within a recording threshold of a recording site, the stethoscope may record an audio signal of the patient. For example, has the identifiable marker (i.e. hand) moved to a correct recording site location? (step 508)

If the stethoscope has not moved within a recording threshold of a recording site body part of patient, repeat step 506. That is, provide additional instructions to the patient to move the stethoscope within a recording threshold of the one of the one or more recording sites of the patient.

If the stethoscope has moved and is positioned at a recording site of a body part of patient, a signal may be recorded based on an audio signal from the stethoscope. Subsequently, the recorded audio signal may be pre-processed to "clean" or filter the audio signal. DSP techniques may be utilized to "clean" the audio signal acquired from stethoscope. This process may be referred to as "pre-processing" or "DSP clean-up" and results in a pre-processed recorded audio signal or pre-processed audio sample. The sample recording may be 5-10 second in length, or as long as required. (step 510)

Is a Signal of Interest (SoI) present in the recorded audio signal? Using Machine Learning (ML) techniques, determine if the Signal of Interest (SoI) is present in the pre-processed audio sample. SoI may be based on heart, lung, bowel, muscle, or skin audio sounds, This step may be referred to as "validation" (step 512)

If the SoI is present, the deep learning system 105 will apply ML techniques to determine if there are any characteristic sounds indicative of a potential ailment or abnormality in the organ being measured, e.g. crackling of lungs. This step may be referred to as "classification" or "symptom classification. (step 514)

Then, repeating steps 502, 504, 506, 510, 512, and 514 for the other/remainder of the recording sites on the body parts of patient 310. That is, repeating, by the diagnostic system, the determination of whether the signal of interest is present in pre-processed audio samples for a remainder of the one or more recording sites on the body parts of patient 310. (step 516)

Analyzing the results and storing results in a deep learning database. Determine if additional measurements of body parts of patient 310 are recommended. (step 518)

If the SoI is not present, instructions may be given to the patient to adjust the location of the stethoscope or to adjust a position of the recording device on the recording site to ensure adequate transduction of a physical phenomenon being recorded by the recording device, e.g. to press a stethoscope more firmly into the recording site. (step 513) Then, repeating steps 506, 508, 510, 512 and 514.

Figure 5C:
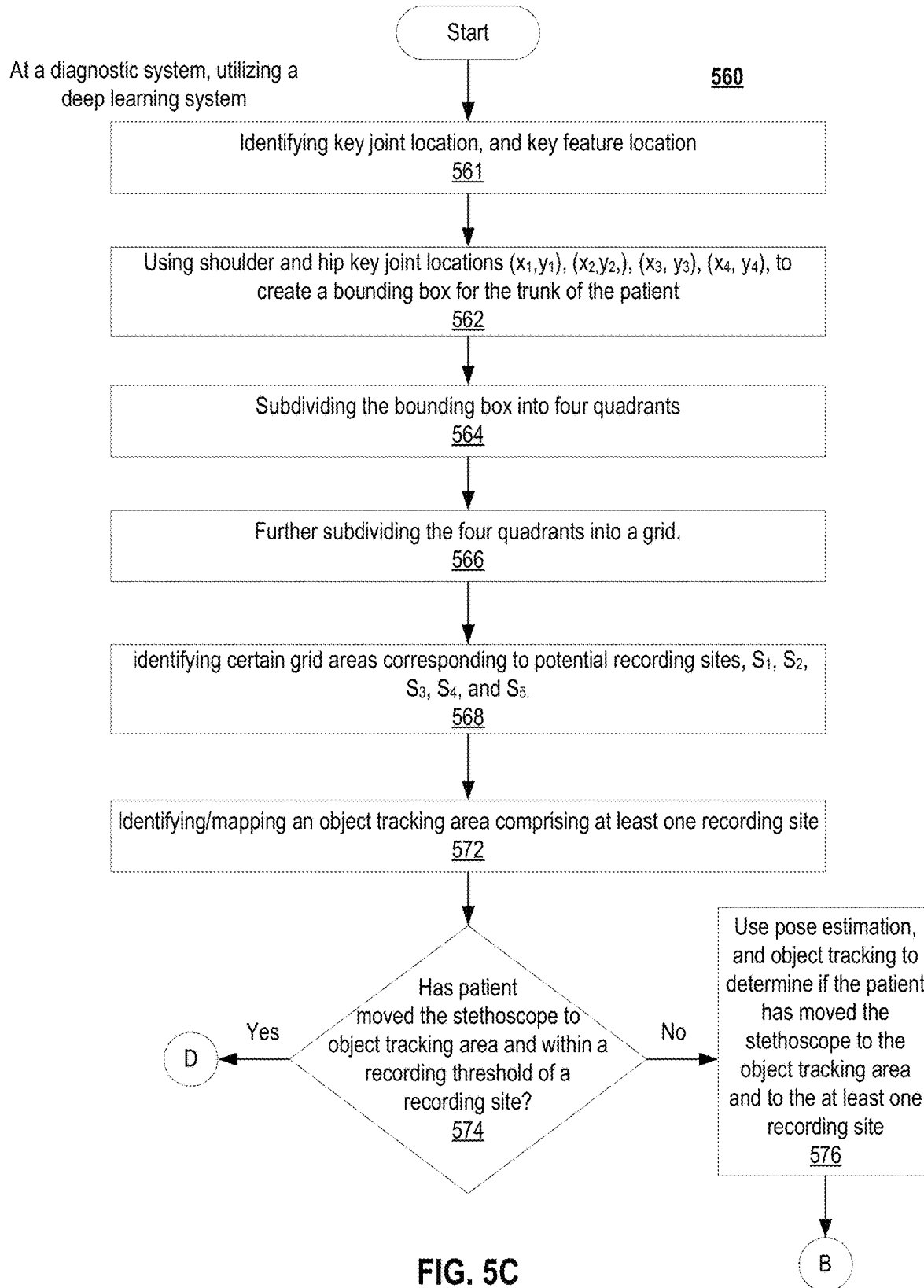
FIG. 5C is a flowchart of an illustrative exemplary method for positioning a stethoscope within a recording threshold to recording sites of body parts of the patient according to embodiments of the present disclosure.

FIG. 5C is a flow chart 560 of an illustrative exemplary method for determining where recording locations are on a patient's body according to embodiments of the present disclosure. Utilizing a computer vision and deep learning algorithms, the method may comprise the following steps:

Identifying key joint location, and key feature location. That is, identifying points of key joints and limbs. (Step 561)

Using shoulder and hip key joint locations $(x_1, y_1)$, $(x_2, y_2)$, $(x_3, y_3)$, $(x_4, y_4)$, to create a bounding box for the trunk of the patient. See FIG. 4A. The bounding box may be the upper half of the torso of a body or the trunk of the body. In other words, the points of key joints and limbs may be used to create a bounding box. This step may be implemented with pose estimation. (Step 562)

Subdividing the bounding box into four quadrants. (see FIG. 4B), (step 564)

Further subdividing the four quadrants into a grid. (see FIG. 4C) (step 566)

Identifying certain grid areas corresponding to potential recording sites, $s_1, s_2, s_3, s_4$, and $s_5$. (see FIG. 4D) (step 568)

Identifying/mapping an object tracking area comprising at least one recording site. (step 572)

Determining if the patient has moved the stethoscope to the object tracking area and to the at least one recording site. (step 574)

If yes, the method continues at step 510: Recording a signal from the stethoscope and pre-processing the audio signal. (DSP clean up). Subsequently, the method continues with step 512: Is a Signal of Interest (SoI) present in the recorded signal? Using Machine Learning (ML) techniques, determine if the Signal of Interest (SoI) is present in the pre-processed audio sample. SoI may be based on heart, lung, bowel, muscle, or skin audio sounds. This step may be referred to as "validation".

If no, use pose estimation, and object tracking to determine if the patient has moved the stethoscope to the object tracking area and to the at least one recording site, then repeat step 506. (step 576)

In embodiments, a time may be calculated at which the selected treatment is expected to show a result and patient feedback may be requested, e.g., as part of a feedback process, to improve diagnosis and treatment reliability. In embodiments, the selected treatment and/or the patient feedback may be used to adjusting one or more of the metrics. For example, based on one or more of the metrics a series of treatment plans may be generated by using an algorithm that combines the metrics. In embodiments, calculating the selected treatment comprises using cost as a factor.

One skilled in the art will recognize that: (1) certain steps may optionally be performed; (2) steps may not be limited to the specific order set forth herein; and (3) certain steps may be performed in different orders; and (4) certain steps may be done concurrently.

In embodiments, one or more computing systems, such as mobile/tablet/computer or the automated diagnostic system, may be configured to perform one or more of the methods, functions, and/or operations presented herein. Systems that implement at least one or more of the methods, functions, and/or operations described herein may comprise an application or applications operating on at least one computing system. The computing system may comprise one or more computers and one or more databases. The computer system may be a single system, a distributed system, a cloud-based computer system, or a combination thereof.

It shall be noted that the present disclosure may be implemented in any instruction-execution/computing device or system capable of processing data, including, without limitation phones, laptop computers, desktop computers, and servers. The present disclosure may also be implemented into other computing devices and systems. Furthermore, aspects of the present disclosure may be implemented in a wide variety of ways including software (including firmware), hardware, or combinations thereof. For example, the functions to practice various aspects of the present disclosure may be performed by components that are implemented in a wide variety of ways including discrete logic components, one or more application specific integrated circuits (ASICs), and/or program-controlled processors. It shall be noted that the manner in which these items are implemented is not critical to the present disclosure.

Figure 6:
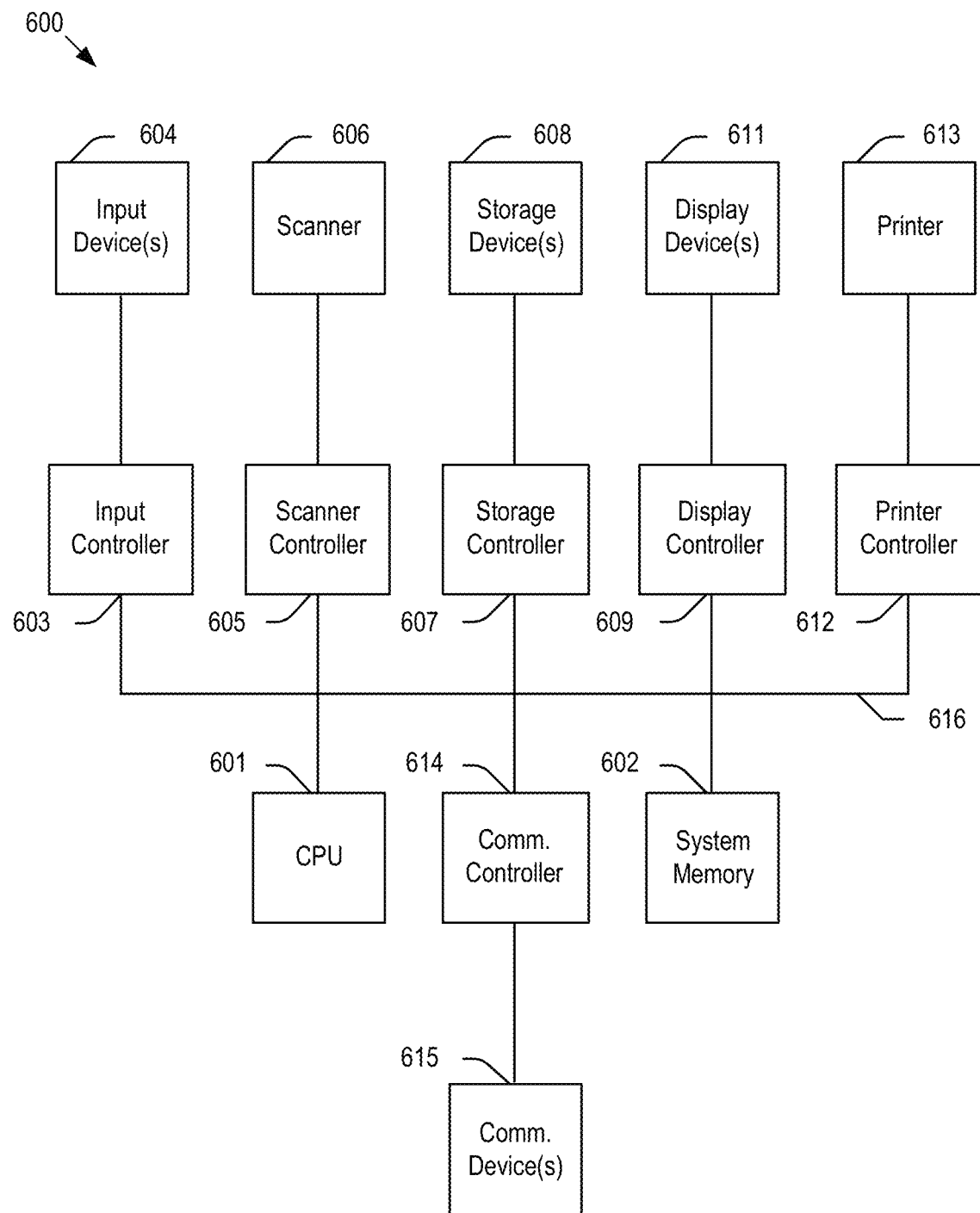
FIG. 6 depicts a simplified block diagram of a computing device/information handling system according to embodiments of the present disclosure.

Having described the details of the disclosure, an exemplary system that may be used to implement one or more aspects of the present disclosure is described next with reference to FIG. 6. Each of patient interface station 106 and automated diagnostic and treatment system 102 in FIG. 1 may comprise one or more components in the system 600. As illustrated in FIG. 6, system 600 includes a central processing unit (CPU) 601 that provides computing resources and controls the computer. CPU 601 may be implemented with a microprocessor or the like, and may also include a graphics processor and/or a floating point coprocessor for mathematical computations. System 600 may also include a system memory 602, which may be in the form of random-access memory (RAM) and read-only memory (ROM).

A number of controllers and peripheral devices may also be provided, as shown in FIG. 6. An input controller 603 represents an interface to various input device(s) 604, such as a keyboard, mouse, or stylus. There may also be a scanner controller 605, which communicates with a scanner 606. System 600 may also include a storage controller 607 for interfacing with one or more storage devices 608 each of which includes a storage medium such as magnetic tape or disk, or an optical medium that might be used to record programs of instructions for operating systems, utilities and applications which may include embodiments of programs that implement various aspects of the present disclosure. Storage device(s) 608 may also be used to store processed data or data to be processed in accordance with the disclosure. System 600 may also include a display controller 609 for providing an interface to a display device 611, which may be a cathode ray tube (CRT), a thin film transistor (TFT) display, or other type of display. System 600 may also include a printer controller 612 for communicating with a printer 613. A communications controller 614 may interface with one or more communication devices 615, which enables system 600 to connect to remote devices through any of a variety of networks including the Internet, an Ethernet cloud, an FCoE/DCB cloud, a local area network (LAN), a wide area network (WAN), a storage area network (SAN) or through any suitable electromagnetic carrier signals including infrared signals.

In the illustrated system, all major system components may connect to a bus 616, which may represent more than one physical bus. However, various system components may or may not be in physical proximity to one another. For example, input data and/or output data may be remotely transmitted from one physical location to another. In addition, programs that implement various aspects of this disclosure may be accessed from a remote location (e.g., a server) over a network. Such data and/or programs may be conveyed through any of a variety of machine-readable medium including, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices.

Embodiments of the present disclosure may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to write program code (i.e., software) and/or to fabricate circuits (i.e., hardware) to perform the processing required.

It shall be noted that embodiments of the present disclosure may further relate to computer products with a non-transitory, tangible computer-readable medium that have computer code thereon for performing various computer-implemented operations. The media and computer code may be those specially designed and constructed for the purposes of the present disclosure, or they may be of the kind known or available to those having skill in the relevant arts. Examples of tangible computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. Embodiments of the present disclosure may be implemented in whole or in part as machine-executable instructions that may be in program modules that are executed by a processing device. Examples of program modules include libraries, programs, routines, objects, components, and data structures. In distributed computing environments, program modules may be physically located in settings that are local, remote, or both.

For purposes of this disclosure, an information handling system may include any instrumentality or aggregate of instrumentalities operable to compute, calculate, determine, classify, process, transmit, receive, retrieve, originate, switch, store, display, communicate, manifest, detect, record, reproduce, handle, or utilize any form of information, intelligence, or data for business, scientific, control, or other purposes. For example, an information handling system may be a personal computer (e.g., desktop or laptop), tablet computer, mobile device (e.g., personal digital assistant (PDA) or smart phone), server (e.g., blade server or rack server), a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communicating with external devices as well as various input and output (I/O) devices, such as a keyboard, a mouse, touchscreen and/or a video display. The information handling system may also include one or more buses operable to transmit communications between the various hardware components.

One skilled in the art will recognize no computing system or programming language is critical to the practice of the present disclosure. One skilled in the art will also recognize that a number of the elements described above may be physically and/or functionally separated into sub-modules or combined together.

It will be appreciated to those skilled in the art that the preceding examples and embodiment are exemplary and not limiting to the scope of the present disclosure. It is intended that all permutations, enhancements, equivalents, combinations, and improvements thereto that are apparent to those skilled in the art upon a reading of the specification and a study of the drawings are included within the true spirit and scope of the present disclosure.

What is claimed is:

1. A method comprising:
    identifying, by a diagnostic system, key joint and feature locations;
    identifying, by a diagnostic system, a grid on a bounding box for a body trunk of a patient, wherein the bounding box comprises one or more recording sites;
    mapping, by the diagnostic system, an object tracking area on the grid of the bounding box;
    determining, by the diagnostic system, if the patient has moved a stethoscope to the object tracking area and within a recording threshold of the one of the one or more recording sites; and
    in response to the stethoscope moving within the recording threshold of the one of the one or more recording sites, recording an audio signal of the patient.

2. The method according to claim 1, wherein the grid on the bounding box is determined by:
    identifying four coordinate points of the bounding box for the body trunk of the patient,
    subdividing the bounding box into four quadrants,
    further subdividing the four quadrants to generate grid areas, and
    identifying certain grid areas corresponding to one of the one or more recording sites.

3. A system comprising:
    an automated diagnostic system comprising a database;
    a deep learning system coupled to the automated diagnostic system;
    computer vision, supported by one or more camera modules, operable to send images of a patient to the automated diagnostic system; and
    a stethoscope operable to detect an audio signal of the patient when positioned within an object tracking area of the patient.

4. The system according to claim 3, wherein the automated diagnostic system, using object tracking and pose estimation and computer vision, determines if the stethoscope is positioned within the object tracking area of the patient.

5. The system according to claim 3, further comprising:
    a patient interface station operable to send and receive information from the automated diagnostic system, the one or more camera modules and the stethoscope.

6. The system according to claim 3, wherein the automated diagnostic system is operable to analyze information provided by the one or more camera modules, the stethoscope and the deep learning system to generate medical measured data of a body part of the patient.

7. The system according to claim 6, wherein the medical measured data of the body part of the patient is communicated to a physician and a deep learning database.

8. The system according to claim 3, wherein the one or more camera modules provide a pose estimate based on time of flight of multiple light signals emitted from each of the one or more camera modules and reflected back to the one or more camera modules.

9. The system according to claim 3, wherein organ being measured is a heart, lung, bowel, muscle, skin or abdomen.

10. The system according to claim 3, wherein the automated diagnostic system identifies a bounding box of a body trunk of the patient and further identifies the object tracking area where at least one recording sites is located.

11. The system according to claim 3, wherein instructions to move the stethoscope are communicated to the patient via haptic feedback sensors.

* * * * *